(12) United States Patent
Spaeth et al.

(10) Patent No.: US 11,929,187 B2
(45) Date of Patent: Mar. 12, 2024

(54) COLLIMATOR CONTROL

(71) Applicant: CARESTREAM HEALTH, INC., Rochester, NY (US)

(72) Inventors: Michael R. Spaeth, Webster, NY (US); James Rydelek, Henrietta, NY (US); Anthony Dirisio, Rochester, NY (US); Dennis J. O'Dea, Victor, NY (US); Craig F. Hofmann, Pittsburgh, PA (US)

(73) Assignee: Carestream Health, Inc., Rochester, NY (US)

( * ) Notice: Subject to any disclaimer, the term of this patent is extended or adjusted under 35 U.S.C. 154(b) by 400 days.

(21) Appl. No.: 17/288,683

(22) PCT Filed: Oct. 31, 2019

(86) PCT No.: PCT/US2019/058994
§ 371 (c)(1),
(2) Date: Apr. 26, 2021

(87) PCT Pub. No.: WO2020/106424
PCT Pub. Date: May 28, 2020

(65) Prior Publication Data
US 2021/0398707 A1    Dec. 23, 2021

Related U.S. Application Data

(60) Provisional application No. 62/769,011, filed on Nov. 19, 2018.

(51) Int. Cl.
*G21K 1/04*    (2006.01)
*A61B 6/06*    (2006.01)

(52) U.S. Cl.
CPC . *G21K 1/04* (2013.01); *A61B 6/06* (2013.01)

(58) Field of Classification Search
CPC ................ G21K 1/04; A61B 6/06; A61B 6/46
See application file for complete search history.

(56) References Cited

U.S. PATENT DOCUMENTS 3,023,314 A * 2/1962 Hura ........................ G21K 1/04
976/DIG. 430

FOREIGN PATENT DOCUMENTS

| JP | 2009-018208 | | 1/2009 | |
|----|-------------|---|--------|---|
| JP | 2009018208 A | * | 1/2009 | ............... A61B 6/06 |

OTHER PUBLICATIONS

International Search Report dated Feb. 27, 2020 for International Application No. PCT/US2019/0058994 filed on Oct. 31, 2019, 2 pages.

* cited by examiner

*Primary Examiner* — David P Porta
*Assistant Examiner* — Casey Bryant

(57) ABSTRACT

An adjustable collimator includes a pair of knobs configured to adjust an aperture size by manipulating one or both of the knobs. The knobs may be disposed at opposite ends of a first shaft. The knobs may be configured to each adjust a same dimension of the aperture or to each adjust a different dimension of the aperture.

14 Claims, 7 Drawing Sheets

COLLIMATOR CONTROL

CROSS REFERENCE TO RELATED APPLICATIONS

This application claims the benefit of and is a U.S. National Phase filing of PCT Application PCT/US2019/058994 filed Oct. 31, 2019 entitled "COLLIMATOR CONTROL", in the name of Spaeth et al., which claims benefit of U.S. Patent Application Ser. No. 62/769,011, filed Nov. 19, 2018, in the name of Spaeth et al., and entitled COLLIMATOR KNOBS AND POLYMER MAGNETIC BRAKE.

BACKGROUND OF THE INVENTION

The subject matter disclosed herein relates to x-ray systems in medical imaging facilities. In particular, the present invention is directed to collimator aperture size control using knobs attached to a collimator as part of a tube head containing an x-ray source and the collimator.

The discussion above is merely provided for general background information and is not intended to be used as an aid in determining the scope of the claimed subject matter.

BRIEF DESCRIPTION OF THE INVENTION

An adjustable collimator includes a pair of knobs configured to adjust an aperture size by manipulating one or both of the knobs. The knobs may be disposed at opposite ends of a first shaft. The knobs may be configured to each adjust a same dimension of the aperture or to each adjust a different dimension of the aperture. An advantage that may be realized in the practice of some disclosed embodiments of the adjustable collimator is easier manual adjustment of the aperture.

In one embodiment, a collimator includes an adjustable aperture and pair of knobs configured to adjust the aperture size by manipulating one or both of the knobs. The knobs are each fixably attached to opposite ends of an elongated linear shaft or rod.

In one embodiment, a collimator includes an adjustable aperture size and a pair of knobs configured to adjust the aperture size by manipulating one or both of the knobs. The knobs are each disposed at opposite ends of a shaft or rod and are configured to each adjust a different dimension of the adjustable aperture.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 62/769,011, filed Nov. 19, 2018, in the name of Spaeth, et al., and entitled COLLIMATOR KNOBS AND POLYMER MAGNETIC BRAKE, which is hereby incorporated by reference herein in its entirety.

Figure 1:
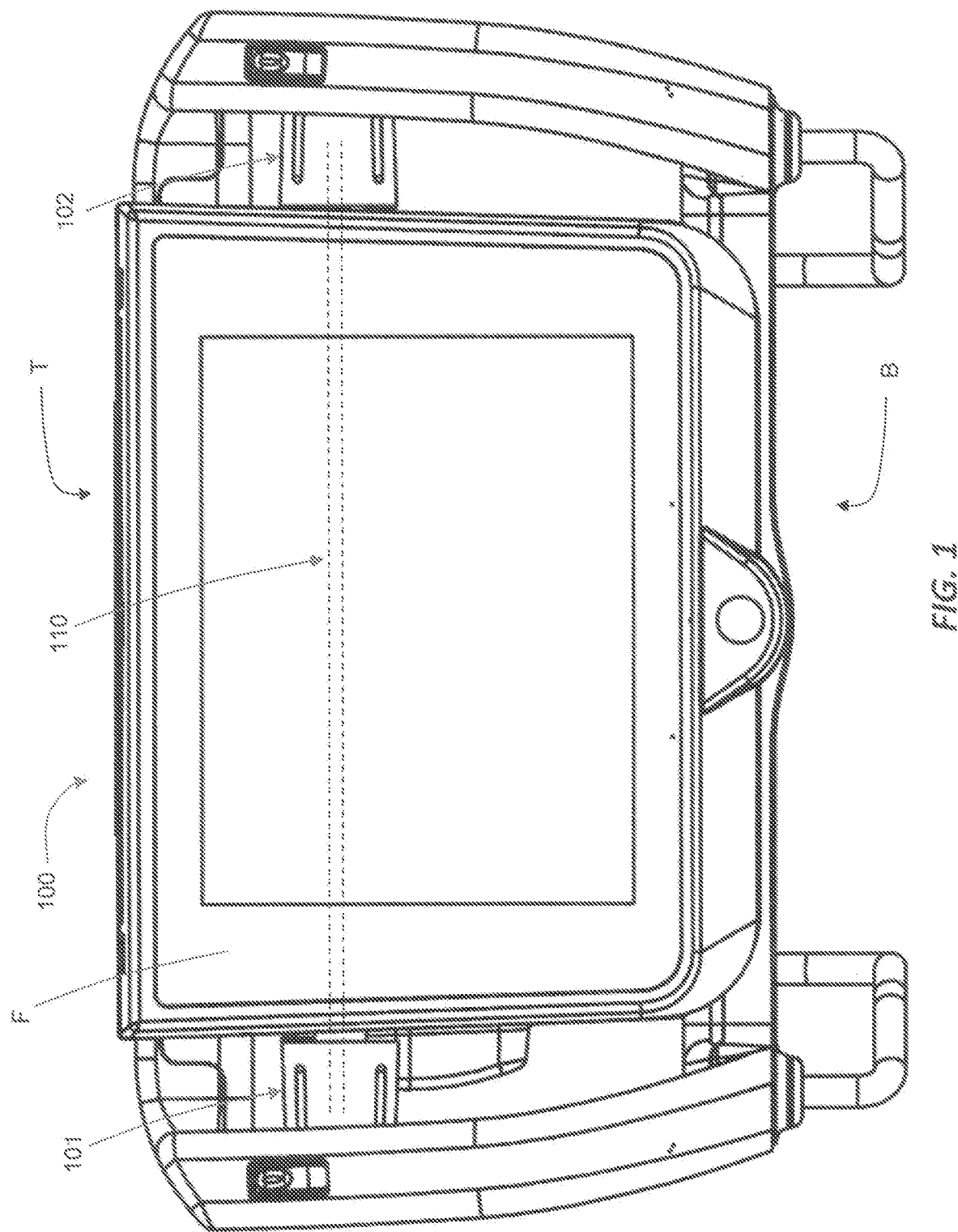
FIG. 1 is a front view of an exemplary collimator.

FIG. 1 shows a front side F of a collimator 100 which may be attached to an x-ray source (not shown) for collimating an x-ray beam generated by the x-ray source. The collimator 100 includes an aperture that may be adjusted in two dimensions using a pair of control knobs 101, 102 on the collimator 100. In general, an x-ray source may be attached to, or near, a top side T of the collimator 100, as viewed in FIG. 1, which emits an x-ray beam aimed downward through the bottom side B of the collimator 100 toward a subject to be radiographically imaged. The aperture inside the collimator 100 shapes the x-ray beam into a desired x-ray beam having adjustable width and length dimensions as the x-ray beam exits the collimator 100 on the bottom side B thereof. In one embodiment, described herein, the collimator knobs 101, 102 may each be fixably attached to a shaft 110 such that manually rotating one of the knobs 101, 102, causes the shaft 110 to rotate and causes the other knob 101, 102, to rotate due do the fixed attachment of the knobs 101, 102 to the shaft 110.

Figure 2:
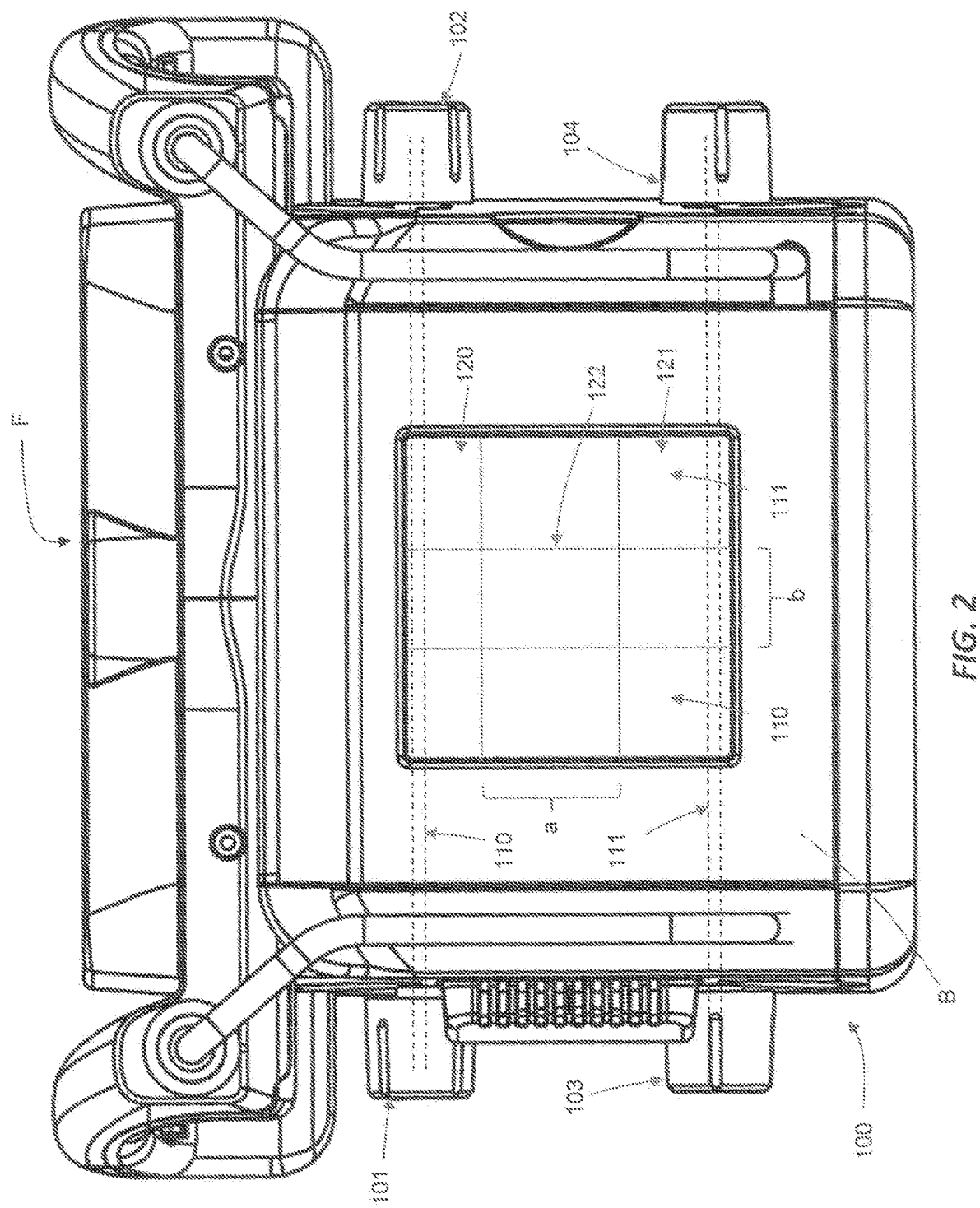
FIG. 2 is a bottom view of the exemplary collimator of FIG. 1.

FIG. 2 is a bottom view of the collimator 100 further illustrating a second pair of control knobs 103, 104, (behind the knobs 101, 102, respectively, in the view of FIG. 1) and a centrally positioned collimator aperture 122. Each of the control knobs 103, 104, is fixably attached to a second shaft 111. One pair of the control knobs, say, 101, 102, may be used to control one dimension of the collimator aperture 122, either a length or width dimension a, b, thereof, and another pair of the control knobs, say, 103, 104, may be used to control the other one of the length and width dimensions a, b, of collimator aperture 122. In one embodiment, described herein, the collimator knobs 103, 104, may each be fixably attached to the shaft 111 such that manually rotating one of the knobs 103, 104, causes the shaft 111 to rotate and causes the other knob to rotate due do the fixed attachment of the knobs 103, 104 to the shaft 111.

In one embodiment, one pair of the control knobs, attached to a common shaft, may be configured to simultaneously move one pair of collimator blades 110, 111, when either of the pair of control knobs is rotated. Manual rotation in one direction of either control knob of the pair may cause the collimator blades 110, 111, to move towards each other, thereby decreasing dimension b of the collimator aperture 122. Manual rotation in an opposite direction of either control knob of the pair may cause the collimator blades 110, 111, to move away from each other, thereby increasing dimension b of the collimator aperture 122. Similarly, another pair of the control knobs, attached to a common shaft, may be configured to simultaneously move another pair of collimator blades 120, 121, when either of the pair of control knobs is rotated. Manual rotation in one direction of either control knob of the pair may cause the collimator blades 120, 121, to move toward each other, thereby decreasing dimension a of the collimator aperture 122. Manual rotation in an opposite direction of either control knob of the pair may cause the collimator blades 120, 121, to move away from each other, thereby increasing dimension a of the collimator aperture 122. In a typical example operation, a user may simultaneously grasp knobs 101 and 103, using one hand for each knob, to rotate both knobs 101, 103, to be able to manually, simultaneously adjust both length and width, or dimensions a and b, of the collimator aperture 122. Similarly a user may simultaneously grasp knobs 102 and 104, using one hand for each knob, to rotate both knobs 102, 104, to be able to manually, simultaneously adjust both length and width, or dimensions a and b, of the collimator aperture 122. Similarly, a user may also simultaneously grasp knobs 101 and 104, or 102 and 103, using one hand for each knob, to rotate both knobs and simultaneously adjust both dimensions of the collimator aperture 122, as described.

Figure 3:
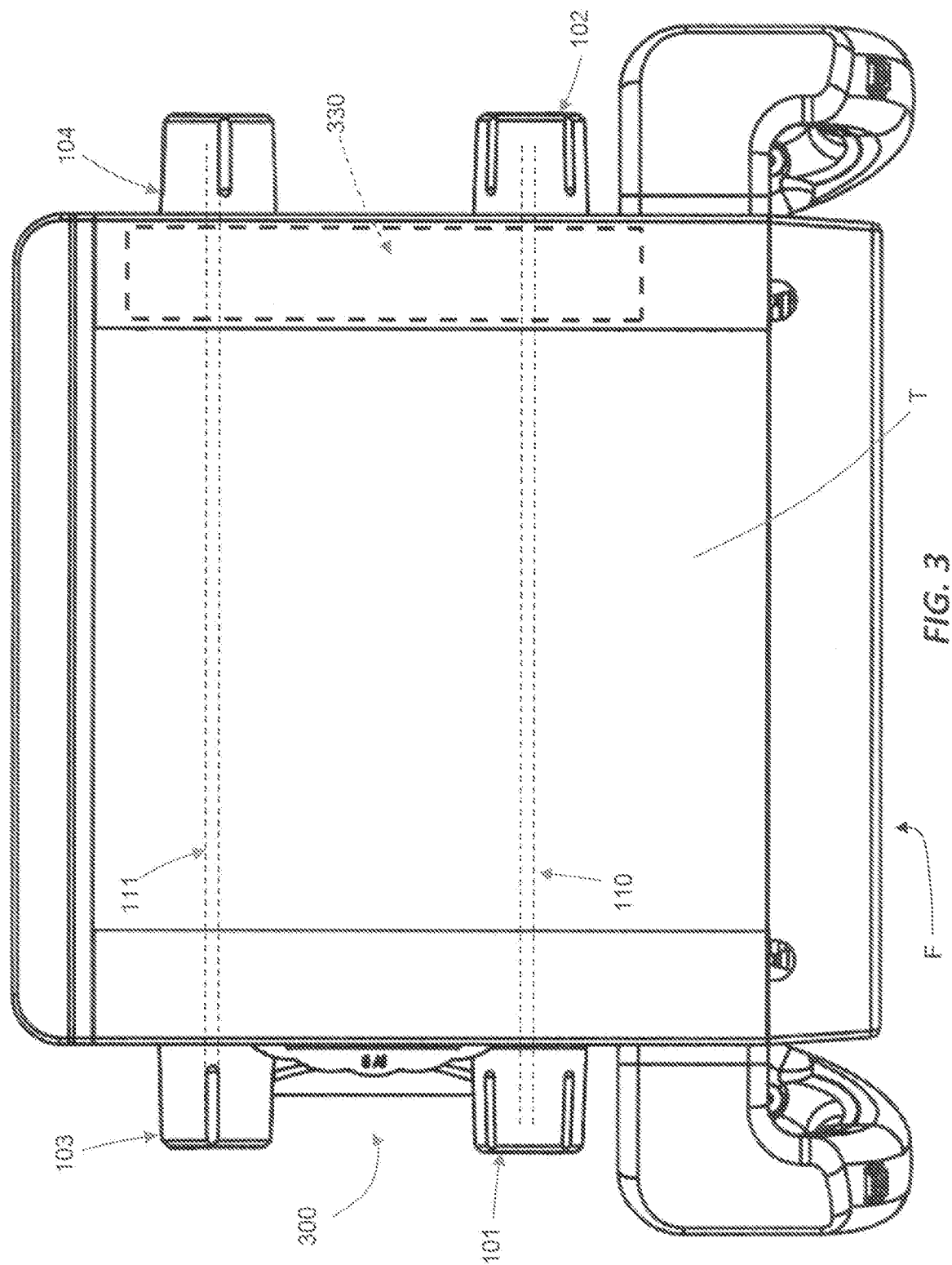
FIG. 3 is a top view of the exemplary collimator of FIG. 1.

FIG. 3 is a top view of an embodiment of a collimator 300 illustrating control knobs 101-104 and shafts 110, 111. In the embodiment of FIG. 3, control knob 101 may be fixably attached to shaft 110 and control knob 103 may be fixably attached to shaft 111 as described herein above with respect to FIGS. 1-2. In the embodiment of FIG. 3, control knob 102 is rotatably attached to shaft 110 and control knob 104 is rotatably attached to shaft 111, whereby rotating control knob 102 does not cause shaft 110 to rotate, and rotating control knob 104 does not cause shaft 111 to rotate. Rather, via assembly 330, described herein (FIGS. 4-6), which is disposed in the collimator 300, rotating control knob 102 causes shaft 111 and control knob 103 to rotate and is configured to adjust one dimension of collimator aperture 122, while rotating control knob 104 causes shaft 110 and control knob 101 to rotate and is configured to adjust another dimension of collimator aperture 122. Similarly, rotating control knob 103 causes shaft 111 and control knob 102 to rotate as well as adjusting one dimension of collimator aperture 122, and rotating control knob 101 causes shaft 110 and control knob 104 to rotate as well as adjusting another dimension of collimator aperture 122. As described herein above, in the embodiment of FIG. 3 each pair of control knobs, 101 & 104 and 102 & 103 rotate together to cause adjustment to the collimator aperture 122 by moving a corresponding pair of collimator blades 110, 111, and 120, 121.

In a typical example operation of the collimator 300 embodiment of FIG. 3, a user may simultaneously grasp knobs 101 and 102, each positioned proximate the front side F of the collimator 300, using one hand for each knob, to rotate both knobs 101, 102, to be able to manually, simultaneously adjust both length and width, or dimensions a and b, of the collimator aperture 122. Similarly a user may simultaneously grasp pairs of knobs 102 and 104, or 101 and 103, using one hand for each knob, to rotate both knobs to be able to manually, simultaneously adjust both length and width, or dimensions a and b, of the collimator aperture 122. Thus, a user is able to adjust both dimensions of the collimator aperture 122 using knobs on either side (left/right) of the collimator 300 or the knobs proximate to the front F of the collimator 300. The shafts 110, 111, are illustrated in FIGS. 1-3 in schematic form. The shafts 110, 111, may include varying radial dimensions along their lengths, and may include other features, such as gears (e.g., FIG. 5) etc., formed therein or attached thereto.

Figure 4:
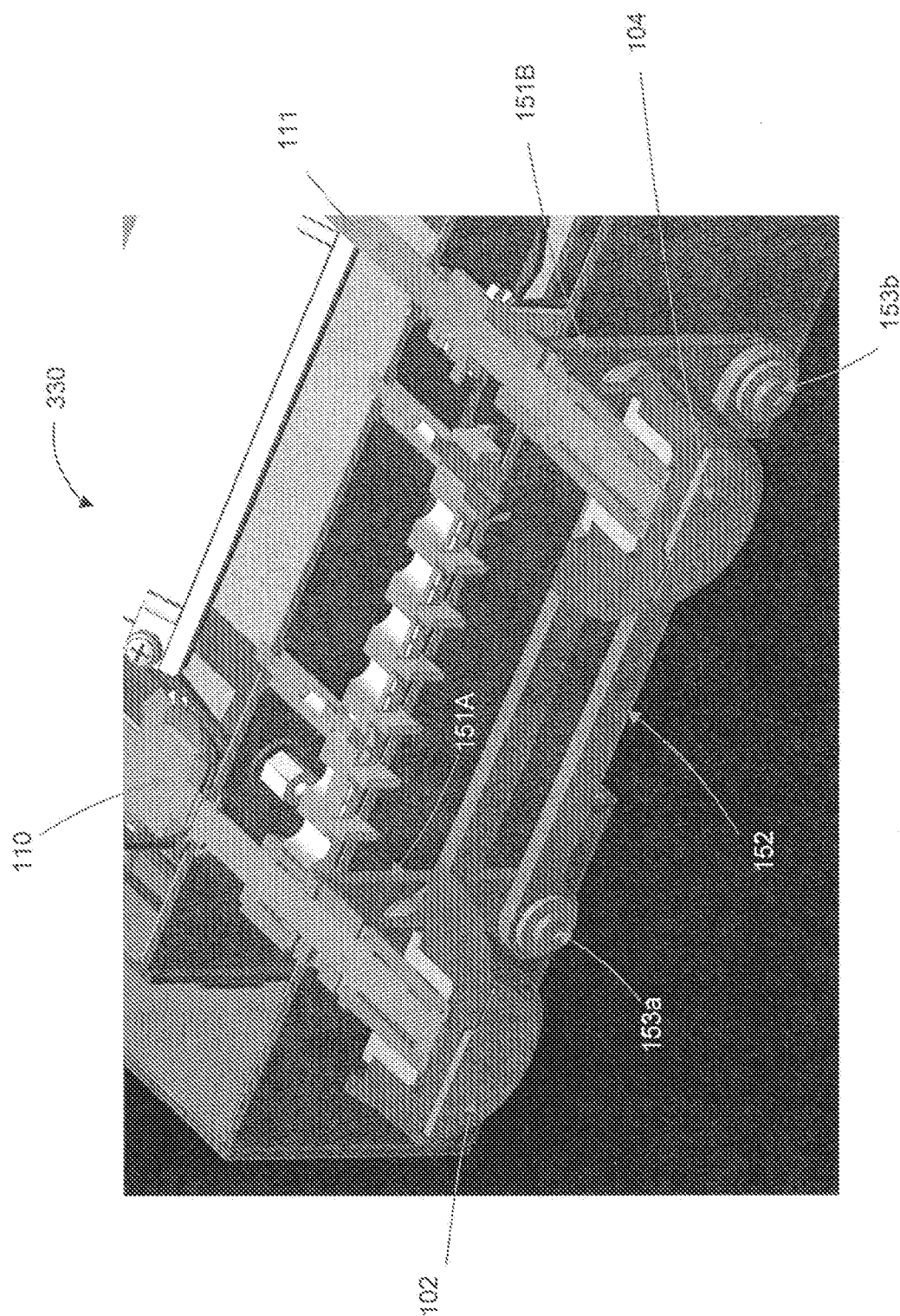
FIGS. 4 and 5 show a cross section of an exemplary assembly for providing advantageous control knob functions.

FIG. 4 is a cross section view of assembly 330 along a plane through the shafts 110, 111 illustrating a portion of assembly 330 which is configured to allow operation of the collimator 300 as described above with reference to the embodiment of FIG. 3. Knobs 102 and 104 are rotatably attached to shafts 110, 111, respectively, and, when rotated, do not cause the respective rotatably attached shaft to rotate. Rather, control knob 102 is fixably attached to a first rigid linear extension 151A using connector 160 and extension 161 (FIG. 6) which are fixably attached to control knob 102, causing rigid linear extension 151A to rotate about the shaft 110 when control knob 102 is rotated. Rigid linear extension 151A is attached to rigid rod or bar 152 using a pivoting coupling 153a. Rigid rod 152 is attached to a second linear rigid extension 151B using another pivoting coupling 153b. Linear rigid extension 151B is fixably attached to shaft 111. Thus, when control knob 102 is manually rotated, shaft 110 is not thereby caused to rotate, and shaft 111 is caused to rotate via the assembly 330 comprising rigid linear extensions 151A-151B, rigid rod 152 and two pivoting couplings 153a,b. Knob 103 (not shown in FIG. 4) is fixably attached to an opposite end of shaft 111 and rotates together with shaft 111. Similarly, when knob 103 is rotated, the assembly 330 causes knob 102 to rotate. As described herein, such rotation of control knobs 102, 103, is configured to adjust one dimension of collimator aperture 122.

Figure 5:
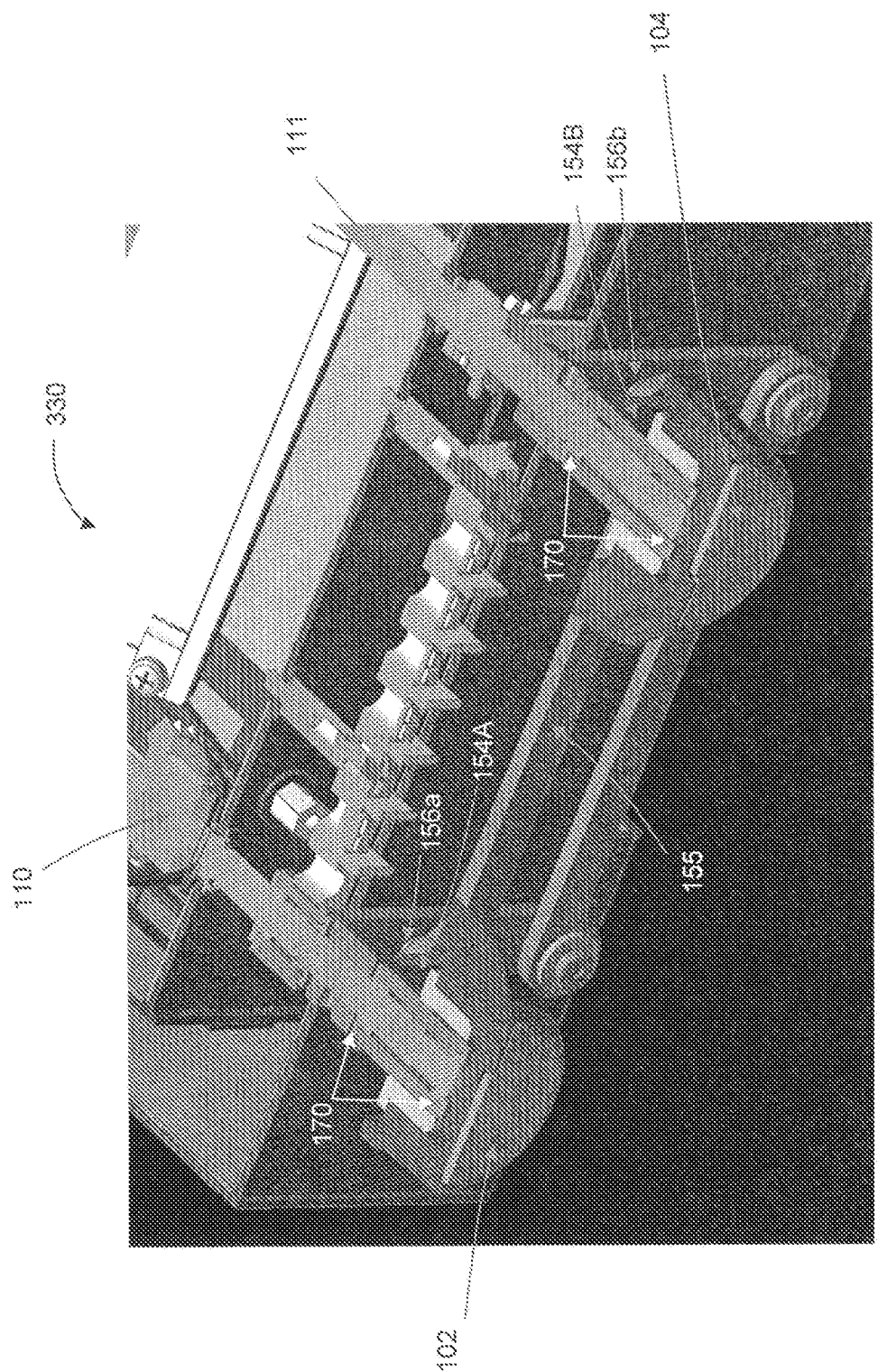

FIG. 5 is a copy of FIG. 4, and will be used to illustrate another portion of assembly 330 which is configured to allow operation of the collimator 300 as described above with reference to the embodiment of FIG. 3. Control knob 104 is fixably attached to rigid linear extension 154B, causing it to rotate about the shaft 111 when control knob 104 is rotated. Rigid linear extension 154B is attached to rigid rod or bar 155 using a pivoting coupling 156b. Rigid rod 155 is attached to linear rigid extension 154A using another pivoting coupling 156a. Linear rigid extension 154A is fixably attached to shaft 110. Thus, when control knob 104 is manually rotated, shaft 111 is not thereby caused to rotate, and shaft 110 is caused to rotate via the assembly 330 comprising rigid linear extensions 154A-154B, rigid rod 155 and two pivoting couplings 156a,b. Knob 101 (not shown in FIG. 5) is fixably attached to an opposite end of shaft 110 and rotates together with shaft 110. Similarly, when knob 101 is rotated, the assembly 330 causes knob 104 to rotate. As described herein, such rotation of control knobs 101, 104, is configured to adjust another dimension of collimator aperture 122. Glide bushings 170 may be used to rotatably attach each control knob 102, 104, to a shaft 110, 111, respectively, to eliminate or minimize friction therebetween. Other mechanisms may be used to assemble assembly 330 to operate in a similar fashion. For example, drive belts+pulleys, linkages, or gears may be used.

Figure 6:
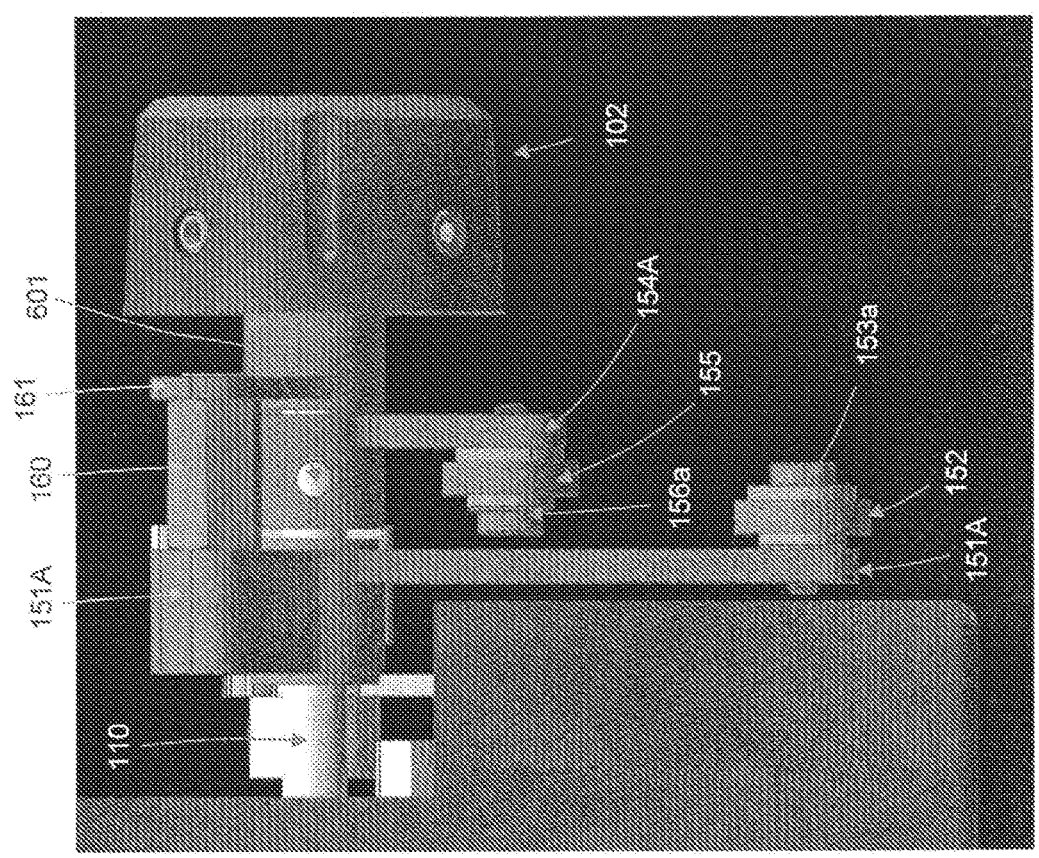
FIG. 6 is a front view of the exemplary assembly for providing advantageous control knob functions.

FIG. 6 shows another view, from a front side of collimator 300, of a portion of the assembly 330 which may be referenced for clarity in view of the description above describing FIGS. 4-5. In the view of FIG. 6, knob 104 is directly behind knob 102 and so is not visible. Rigid linear extension 151A is fixably attached to knob 102 but not to shaft 110. Rigid linear extension 151A freely rotates about shaft 110. Rigid linear extension 154A is fixably attached to shaft 110, using set screw 601, but not to knob 102. Complementary couplings are used similarly to attach similar components to knob 104, as described herein.

Figure 7:
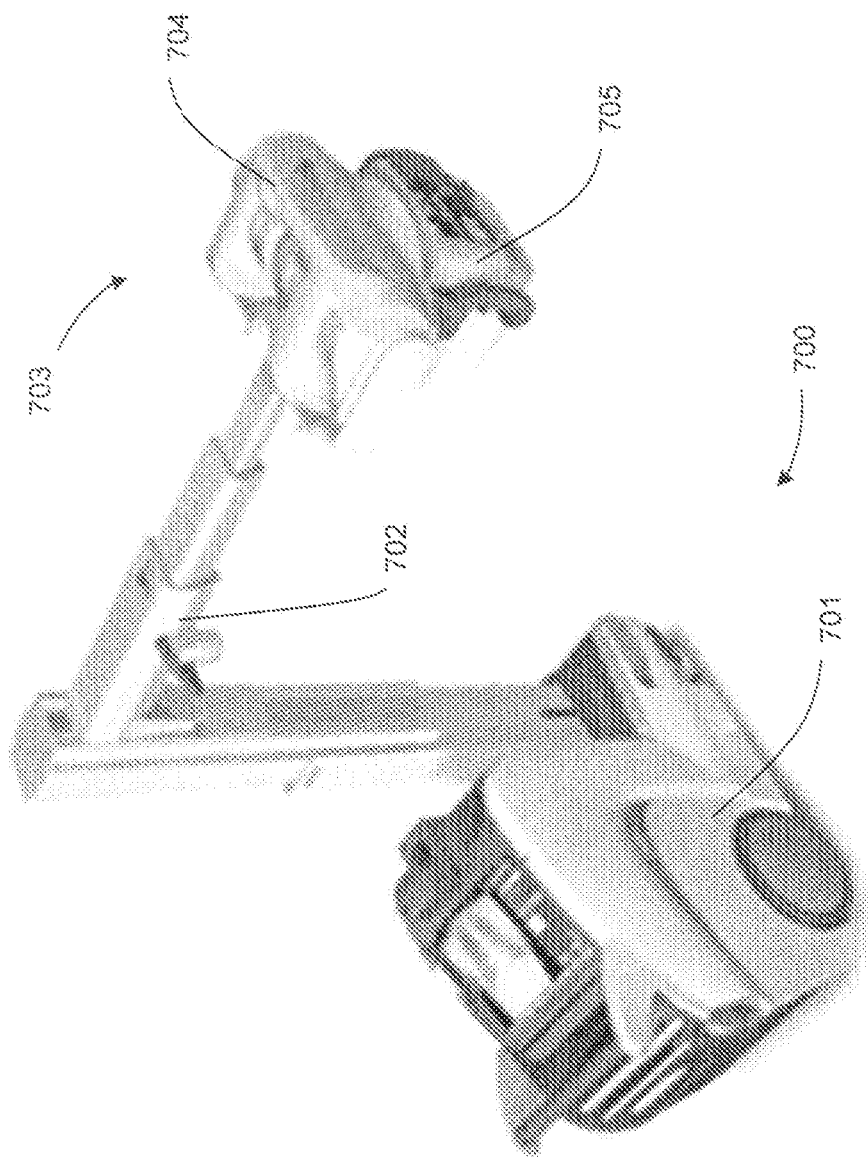
FIG. 7 shows an example mobile x-ray cart having a tube head utilizing the exemplary collimator having the exemplary assembly described herein.

FIG. 7 shows an exemplary mobile x-ray system 700 having a base 701, an adjustable control arm 702 rotatably attached to the base 701, which control arm supports a tube head 703, which tube head includes an x-ray source 704 and a collimator 705, which collimator may include the embodiment of collimator 100 or collimator 300 described herein. The collimators 100, 300, may also be used with non-mobile in-room x-ray systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A collimator comprising:
an adjustable aperture size; and
a first pair of knobs configured to adjust the aperture size by manipulating one or both of the first pair of knobs;
wherein the first pair of knobs are each attached to opposite ends of a first shaft, and
wherein each of the first pair of knobs is configured to adjust a different dimension of the adjustable aperture.

2. The collimator of claim 1, wherein the different dimensions of the adjustable aperture comprise orthogonal length and width dimensions.

3. The collimator of claim 2, further comprising two pairs of collimator blades, wherein the first pair of knobs are each configured to move a different pair of the collimator blades.

4. The collimator of claim 3, wherein the collimator comprises a front side having two non-adjacent opposing edges, and two sidewalls each adjacent one of the two opposing edges, and wherein the opposite ends of the shaft each terminate near a different one of the sidewalls.

5. The collimator of claim 3, further comprising a second pair of knobs configured to adjust the aperture size by manipulating one or both of the second pair of knobs, wherein the second pair of knobs are each attached to opposite ends of a second elongated linear shaft or rod, and wherein each of the second pair of knobs is configured to adjust a different dimension of the adjustable aperture.

6. The collimator of claim 5, wherein a first terminal end of the first shaft and a first terminal end of the second shaft both terminate proximate a common first side of the collimator.

7. The collimator of claim 6, wherein a second terminal end of the first shaft and a second terminal end of the second shaft both terminate proximate a common second side of the collimator different from the first side of the collimator.

8. The collimator of claim 5, wherein a first one of the first pair of knobs is fixably attached to a first end of the first shaft, and wherein a second one of the first pair of knobs is rotatably attached to a second end of the first shaft.

9. The collimator of claim 8, wherein a first one of the second pair of knobs is fixably attached to a first end of the second shaft, and wherein a second one of the first pair of knobs is rotatably attached to a second end of the second shaft.

10. The collimator of claim 1, wherein a first one of the first pair of knobs is fixably attached to a first end of the first shaft, and wherein a second one of the first pair of knobs is rotatably attached to a second end of the first shaft.

11. A method of operating a collimator, the method comprising:
providing a collimator aperture having a manually adjustable size;
attaching a pair of knobs each to an opposite end of a shaft, the pair of knobs for manually adjusting the aperture size; and
adjusting two different dimensions of the collimator aperture by manipulating both of the pair of knobs, wherein the pair of knobs is each configured to adjust a different dimension of the collimator aperture.

12. The method of claim 11, further comprising adjusting orthogonal length and width dimensions of the collimator aperture.

13. The method of claim 12, further comprising moving one pair of collimator blades by manipulating one of the pair of knobs.

14. The method of claim 11, further comprising fixably attaching a first one of the pair of knobs to a first end of the shaft, and rotatably attaching a second one of the pair of knobs to a second end of the shaft.

* * * * *